| United States Patent [19] | [11] Patent Number: 4,478,984 |
| Bryan | [45] Date of Patent: Oct. 23, 1984 |

[54] SYNTHESIS OF BENZHYDRYLAMINE RESINS

[75] Inventor: William M. Bryan, West Chester, Pa.

[73] Assignee: SmithKline Beckman Corporation, Philadelphia, Pa.

[21] Appl. No.: 535,184

[22] Filed: Sep. 23, 1983

[51] Int. Cl.$^3$ .............................................. C08F 32/06
[52] U.S. Cl. ............................. 525/333.6; 525/359.2; 525/375; 525/333.2
[58] Field of Search ................... 525/359.2, 375, 333.2, 525/333.6

[56] References Cited

U.S. PATENT DOCUMENTS 3,773,718  11/1973  Klebe et al. ...................... 525/359.2

OTHER PUBLICATIONS

P. Pietta et al., J. Org. Chem. 39 44, (1974).
R. Orlowski et al., J. Org. Chem. 41 3701, (1976).
P. Pietta et al., Chemical Communications 650, (1970).

*Primary Examiner*—Paul R. Michl
*Assistant Examiner*—Alex H. Walker
*Attorney, Agent, or Firm*—William H. Edgerton; Richard D. Foggio; Alan D. Lourie

[57] ABSTRACT

N-(α-Chlorobenzyl)-phthalimide is condensed with a styrene resin in the presence of stannic chloride to give, after splitting the protective imide, benzhydrylamine resin for use in solid phase peptide synthesis.

3 Claims, No Drawings

SYNTHESIS OF BENZHYDRYLAMINE RESINS

This invention relates to the preparation of certain benzhydrylamine polystyrene resins and intermediates therefor. Such benzhydrylamine resins are of value in the field of the solid phase peptide synthesis (SPPS) of peptide C-α-carboxamides. In these chemical sequences, amino acids are successively attached to a solid insoluble support resin to build a peptide chain.

Such benzhydrylamine resins are known in the art as BHA resins or modified Merrifield resins.

BACKGROUND OF THE INVENTION

A review of the development of solid phase peptide synthesis is available in "Peptide Synthesis", 2nd Ed., M. Bodanszky et al., John Wiley (1976) Chapter Seven, or "The Peptides: Analysis, Synthesis, Biology", Gross, Meienhoffer, Academic Press (1979) Vol. 2, Chapter 1. Originally, chloromethylation of a styrene-divinylbenzene copolymer using monochloromethyl ether in the presence of tin chloride gave a chloromethylphenyl resin which was initially attached to a N-protected amino acid by an ester linkage.

Later for the synthesis of peptide amides, the resin was acylated using a benzoyl halide in a Friedel-Krafts reaction to give benzoylphenyl resin which was converted to a benzhydrylamine resin by reductive amination such as using a Leuckart reaction [J. Hruby et al., J. Org. Chem., 42 3552 (1977), or P. Pietta et al., J. Org. Chem. 39 44 (1974)]. This reaction, or variations of it, has proved useful to the peptide chemist. p-Methylbenzhydrylamine resins, G. R. Matsueda et al., "Peptides", Vol. 2, 45 (1981); p-methoxybenzhydrylamine resins, R. Orlowski et al., J. Org. Chem. 41 3701 (1976); p-nitrobenzhydrylamine resins, R. Colombo, J.C.S. Chem. Comm. 1981 1012; or o,p-dimethoxybenzhydrylamine resin have been used to efforts to improve the procedure. These resins were prepared to increase the lability of the peptide-resin bond, not to improve the overall procedure. Most were made by the reaction sequence described above.

Only the Leuckart reduction method yielded a usable product, M. Christensen et al., Acta Chemica Scandinavica B 35 (1981) 573 or R. Walter et al., J. Org. Chem. 41 3701 (1974). This method has a number of disadvantages, such as poor purity which is especially due to admixture of unreactive keto material, high cost, low and variable yields, long time of chemical throughput and lack of predetermination of the degree of polystyrene substitution.

The present invention contributes to the solution of this prior art problem.

DESCRIPTION OF THE INVENTION

The overall reaction sequence which uses the improved chemical reactions and intermediates of this invention is illustrated by the following:

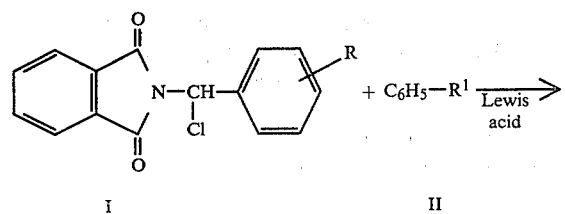

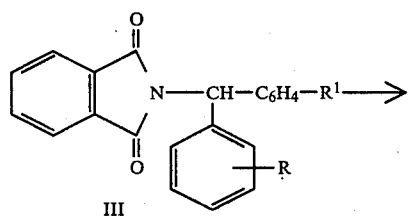

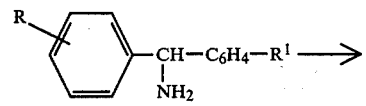

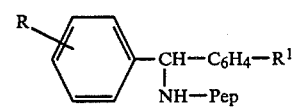

in which:
R is hydrogen, methyl, methoxy or nitro;
R¹, taken with the C₆H₄ to which it is attached, is a polystyrene resin known to the SPPS art; and
Pep is a peptide chain or residue thereof known to the SPPS art.

The intermediates of structure III and the reaction sequence, I+II→IV, constitute key elements of this invention.

N-(α-Chlorobenzyl)-phthalimide (I) is reacted with a styrene based polymer which is known to be useful in solid phase peptide syntheses. The reaction is usually carried out in an organic solvent which is chemically inert under the reaction conditions but in which the reactants are sufficiently soluble to allow reaction. The polystyrene is not, of course, substantially soluble. Such solvents are the halogenated hydrocarbons such as dichloroethane, methylene chloride, chloroform, carbon tetrachloride or tetrachloroethylene. Alternatively, the reaction may be run in the presence of a strong acid such as trifluoromethane sulfonic acid or hydrogen fluoride. The reaction mixture is stirred at room temperature until the desired extent of reaction is reached, most often from 1–8 hours. A time of 2 hours is most useful.

The reaction is carried out in the presence of a Lewis acid such as tin (IV) chloride, antimony (V) chloride, iron (III) chloride or zinc (II) chloride. Tin (IV) chloride gives the best yield at a 2 hour time of reaction as well as a colorless product.

The quantities of the reactants are usually chosen by the operator to achieve his purpose but usually the imide reactant (I) is used in from about 0.5–4 mmoles per gram of styrene polymer. The Lewis acid catalyst is conveniently used as a two fold excess over the imide reagent.

The sole source of nitrogen in the first reaction product (III) arises from the phthalimide condensation reaction. For this reason, the reactive centers on the resulting phthalimide-phenylmethyl resin (PPM) are easily assayed by nitrogen analysis.

The polystyrene resin which is usually used is commercially available styrene-1-2% divinylbenzene copolymer.

The desired product is isolated by washing the resin after the reaction is complete to remove unreacted phthalimide and catalyst.

The PPM resin from the first step of the sequence (III) is heated at reflux in a 10% solution of anhydrous hydrazine in ethanol using a concentration of 10–50 ml of solvent-hydrazine for each gram of PPM resin. Other solvents may be used. The mixture is usually heated from 10–24 hours but 16–18 hours is sufficient. The benzhydrylamine resin is then washed, dried and analyzed by infrared spectrum to determine if any imide is unreacted. The BHA resin (IV) is, then, used in solid phase peptide synthesis as known to the art. The overall reaction sequence can be carried out in about 24 hours using inexpensive and readily available starting materials.

The following examples are designed to illustrate the operation of this invention but not to limit its scope. All temperatures are Centigrade.

EXAMPLE 1

A mixture of 26.0 g (0.1285 m) of benzyl phenyl sulfide, 17.5 g (0.1285 m) of N-chlorosuccinimide and 300 ml of carbon tetrachloride was stirred at room temperature for 4 days. The mixture was filtered. The filtrate was concentrated to give 30.3 g of yellow oil, α-chlorobenzyl phenyl sulfide. This product (30.2 g, 0.1285 m) was reacted without purification with 24.29 g (0.1285 m) of potassium phthalimide in 67 ml of dimethylformamide at 90° overnight with stirring. The mixture was poured into 650 ml of water. The resulting solid was collected and dissolved in 600 ml of methylene chloride. The washed and dried extract was evaporated to give 34.4 g of brown syrup which was treated with charcoal to give 18 g (40.8%) of N-[α-(phenylthio)benzyl]phthalimide, m.p. 97°–99°. A mixture of 18.09 g (0.052 m) of the phenylthio compound, 7.3 g of 97% sulfuryl chloride and 125 ml of methylene chloride was prepared and stirred at room temperature for 3 hours, concentrated on a rotary evaporator and co-evaporated with petroleum ether three times. The resulting solid, 11.65 g (83%) of N-(α-chlorobenzyl)phthalimide, was identical with that of J. W. Worley, J. Org. Chem. 44, 1176 (1979).

A mixture of 5.42 g (20 mmole) of N-(α-chlorobenzyl)phthalimide, 10 g of washed and dried polystyrene-1%-divinylbenzene ("Biobeads" SX-1 Bio-Rad Laboratory), 5.21 g (40 mmole) of stannic chloride and 250 ml of dichloroethane was stirred at 25° for 2 hours. The mixture was filtered and the resin washed five times each with methylene chloride, absolute ethanol, 1:1 ethanol-water, water and methylene chloride (200 ml each). The resin was dried under vacuo overnight. Nitrogen analysis gave 1.26% N or 0.9 mmole of nitrogen per gram of resin. The carbonyl band in the infrared spectrum absorbed at 1710 and 1775 cm$^{-1}$, 12.6% yield.

A mixture of 10 g of the PPM resin and 200 ml of 10% anhydrous hydrazine in ethanol was heated at reflux overnight, then filtered hot. The resin was washed with 5×200 hot ethanol and 5×200 hot methanol, then dried under vacuo to give 7.52 g of benzhydrylamine polystyrenedivinylbenzene resin (BHA resin) which had no carbonyl absorption in the infrared spectrum.

EXAMPLE 2

A series of runs of the condensation reaction of Example 1 with varying quantities of N-(α-chlorobenzyl)phthalimide was carried out. Each reaction was run in a 250 ml flask at ambient temperature with stirring using 1.00 g of polystyrene resin in 25 ml of dichloroethane. To each flask the chloro compound and solvent were added. After 10 minutes, the stannic chloride was added neat. After 2.0 hours, the resin was separated, washed with 5×20 methylene chloride, 3×20 ethanol, 3×20 aqueous ethanol and 3×20 ethanol and dried in vacuo.

| N—(α-Chlorobenzyl)-phthalimide | | Stannic Chloride | | Product (PPM resin) | |
|---|---|---|---|---|---|
| mmole | g | mmole | g | % N | mmole N/g |
| 0.5 | 0.135 | 1.0 | 0.26 | 0.21 | 0.15 |
| 1.0 | 0.27 | 2.0 | 0.52 | 0.59 | 0.46 |
| 1.5 | 0.41 | 3.0 | 0.78 | 0.96 | 0.68 |
| 2.0 | 0.54 | 4.0 | 1.04 | 1.32 | 0.94 |
| 2.25 | 0.68 | 4.5 | 1.17 | 1.58 | 1.12 |
| 2.00 | 0.54 | 4.0 | 1.04 | 1.34 | 0.96 |
| 1.75 | 0.47 | 3.5 | 0.91 | 1.27 | 0.90 |
| 1.00 | 0.27 | 2.0 | 0.52 | 0.55 | 0.71 |

These experiments demonstrate the reproducable nature of the reaction and the ease with which the degree of substitution can be controlled.

EXAMPLE 3

Polystyrene resin (200 mg) was placed in each of 4 test tubes along with 0.11 g (0.4 mmole) of the chloro compound and 0.30 ml of dichloroethane, then, after the respective Lewis acid catalyst was added, the reaction was allowed to stir at room temperature for two hours. The resin was filtered off, washed and dried as above.

| Catalyst | Amount (1.6 mmole) | % N | mmole N/G of resin |
|---|---|---|---|
| AlCl$_3$ | 0.21 g | N.R. | N.R. |
| FeCl$_3$ | 0.26 g | 0.84 | 0.60 |
| CuCl | 0.16 g | N.R. | N.R. |
| ZnCl$_2$ | 0.22 g | 0.13 | 0.09 |
| SbCl$_6$ | 0.48 g | 0.50 | 0.36 |
| SnCl$_4$ | 0.42 g | 1.29 | 0.92 |

This experiment demonstrated the versatility of Lewis acid which can be used.

EXAMPLE 4

The reaction of Example 1 is repeated with 0.13 m of p-methoxybenzyl phenyl sulfide and N-bromosuccinimide to give N-[α-(phenylthio)-p-methoxybenzyl]phthalimide and, then, the N-(α-chloro-p-methoxybenzyl)phthalimide using sulfuryl chloride. The p-methyl and p-nitro congeners are prepared similarly.

Each of these is reacted with polystyrene resin-stannic chloride as described in Example 1 to give the p-methoxy, p-methyl or p-nitro-BP-resins of this invention.

What is claimed is:
1. The method of preparing a BHA resin compound of the formula:

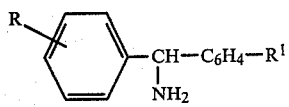

in which:

$R_1$ is hydrogen, methyl, methoxy or nitro; and $R^1$, taken with the $C_6H_4$ to which it is attached, is a polystyrene, comprising reacting a compound of the formula:

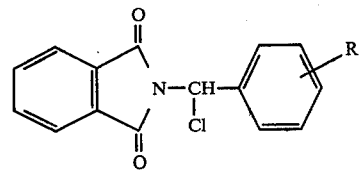

in which:

R is as defined above, with a polystyrene containing resin in the presence of a Lewis acid to give a PB resin compound of the formula:

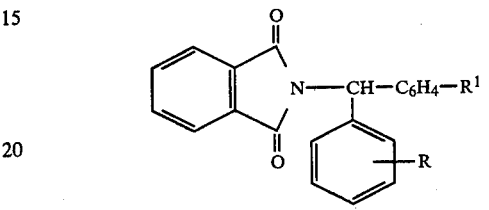

in which R and $R^1$ are as defined above, and, reacting said PB resin compound with hydrazine.

2. The method of claim 1 in which R is hydrogen and the Lewis acid is stannic chloride.

3. The method of claim 1 in which R is p-methoxy.

* * * * *